United States Patent [19]

Hershberger

[11] 4,322,497
[45] Mar. 30, 1982

[54] PROCESS FOR TRANSDUCING ESCHERICHIA COLI K12 χ1776

[75] Inventor: Charles L. Hershberger, New Palestine, Ind.

[73] Assignee: Eli Lilly and Company, Indianapolis, Ind.

[21] Appl. No.: 911,852

[22] Filed: Jun. 2, 1978

[51] Int. Cl.$^3$ ............................................. C12N 15/00
[52] U.S. Cl. ..................................... 435/172; 435/849
[58] Field of Search ........................................ 435/172

[56] References Cited

U.S. PATENT DOCUMENTS 4,190,495 2/1980 Curtiss .................................. 435/172

OTHER PUBLICATIONS

Curtiss et al., Miami Winter Symp. 1977, 13, Mol Cloning Recomb. DNA, pp. 99–114.
Derwent Abstract 25578A (Abstracting German Offenlegungsschrift 26 44 432.

Primary Examiner—Alvin E. Tanenholtz
Attorney, Agent, or Firm—Nancy J. Harrison; Arthur R. Whale

[57] ABSTRACT

A method of providing maximum frequencies of transduction with *Escherichia coli* strains, such as *E. coli* K12 χ1776, that are transduced poorly in the exponential growth phase, which comprises transducing the culture in the stationary phase of growth. *E. coli* K12 χ1776 strains modified by transduction using this method are useful as EK2 hosts for biological containment.

3 Claims, 1 Drawing Figure

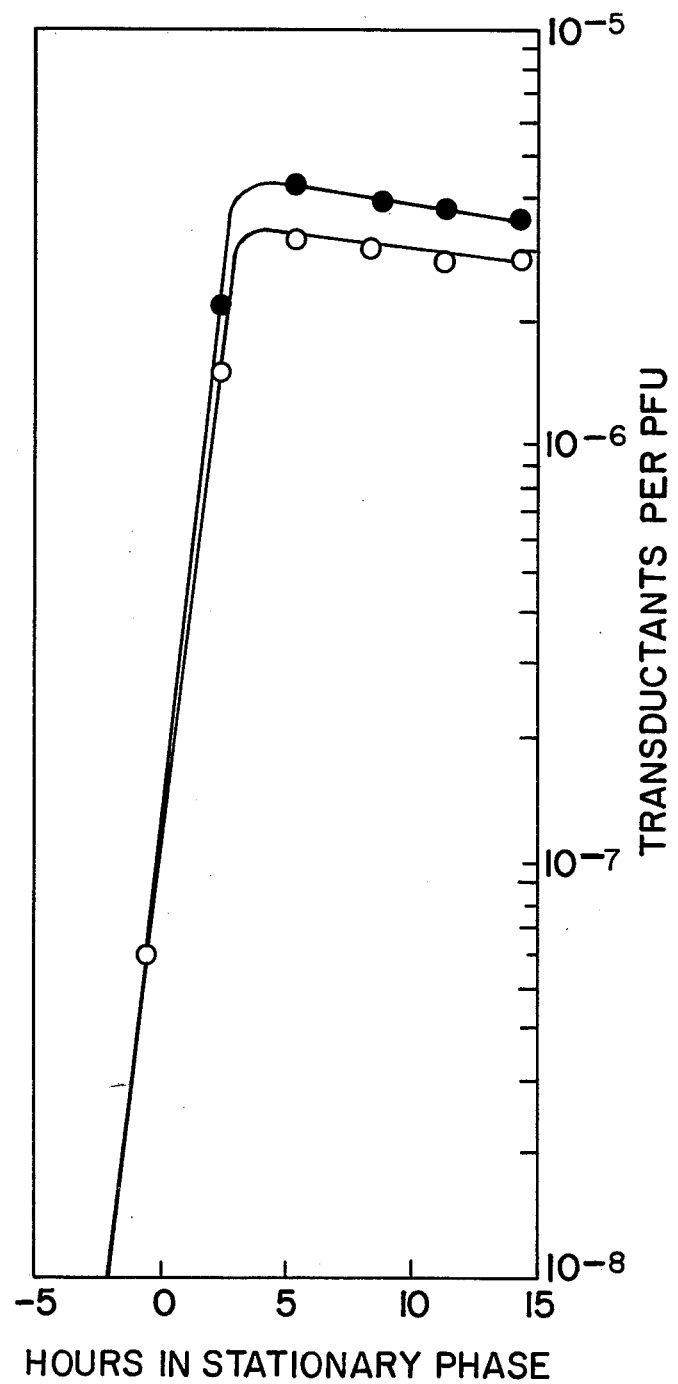

PROCESS FOR TRANSDUCING ESCHERICHIA COLI K12 χ1776

BACKGROUND OF THE INVENTION

Developments in molecular biology have provided researchers with tools for constructing recombinant DNA in vitro. Several applications of this technique include: (1) investigating chromosome structure; (2) analyzing mechanisms of genetic regulation, (3) isolating specific genes or segments of DNA, and (4) constructing intergeneric chimeras with unique properties and biosynthetic capabilities. Recent reports of the production of insulin and somatostatin using techniques of recombinant DNA are examples of the significant impact of recombinant DNA research.

To assist in understanding the new terminology of this field, the following definitions of terms used throughout this application are provided:

DNA—Deoxyribonucleic acid;

Bacteriophage—any of the viruses that infect bacterial cells; also known as phage; a particle composed of a piece of DNA enclosed and contained within a protein head portion and having a tail and tail fibers composed of protein;

Transducing phage—A bacteriophage that carries fragments of bacterial chromosomal DNA and transfers this DNA on subsequent infection of another bacterium;

Transduction—Bacteriophage-mediated transfer of bacterial genetic information;

Donor—In transduction, the strain used for propagation of phage to be used in transducing markers to a recipient;

Recipient—In transduction, the strain which receives genetic markers by transduction;

Chimera—A strain carrying DNA which contains genetic information from two different sources;

Transductant—A new strain generated by transduction;

Auxotroph Mutant—A mutant which requires one or more growth factors in the medium not required by the parent cells;

Phototroph—An organism which does not require a growth factor in the media;

Phenotype—The observable character of an organism controlled by the gene;

Genome—The total genetic endowment of a species;

pfu—Plaque-forming units, i.e., the number of infective bacteriophage;

moe—Multiplicity of exposure; i.e., the number of pfu divided by the number of cells;

NIH Guidelines—The National Institutes of Health safety recommendations for research involving recombinant DNA molecules;

P1, P2, P3, and P4—Physical-containment levels established by the NIH Guidelines; P1 being the lowest level of containment and P4 being the most stringent level of containment;

EK1, EK2, and EK3—Biological-containment levels established by the NIH Guidelines; EK1 being the lowest level of containment and EK3 being the most stringent level of containment.

Experiments with recombinant DNA are regulated by guidelines that have been established by the NIH. Many important experiments require effective containment to reduce the probability that experimental chimeras will escape from the laboratory. Under the current NIH guidelines biological containment is to be used in combination with physical containment for safety purposes. Biological containment requires the use of a crippled strain of *Escherichia coli*, such as *E. coli* K12. *E. coli* K12 is a laboratory-adapted strain unable to survive more than 48 hours in the human intestinal tract. Several planned mutational defects in *E. coli* K12 have resulted in a self-destructing *E. coli* strain called *E. coli* K12 χ1776. This strain is acceptable for use in experiments requiring an EK2 host-vector system. *E. coli* K12 χ1776 is unable to synthesize its own cell wall or to replicate its DNA outside a carefully controlled laboratory environment. In addition to the fact that its ability to survive in the human intestinal tract is further reduced, *E. coli* K12 χ1776 is also extremely sensitive to (1) sunlight, (2) moderately warm temperatures and (3) detergents and chemicals which are frequently found in sewers and polluted waters. For this reason, *E. coli* K12 χ1776 (herein called χ1776) has been approved as an EK2 host for biological containment.

In the combination of physical and biological containment outlined in the NIH guidelines, an EK2 host can be used in experiments at a reduced level of physical containment compared with similar experiments using an EK1 host.

The normal experimental protocol for transducing *E. coli* strains such as *E. coli* K12 involves accomplishing transduction during the exponential growth phase. Because of the importance of *E. coli* K12 χ1776, the ability to transduce genetic markers into this strain is extremely important. Derivatives of χ1776 for this purpose, however, could not be isolated using the procedure for transducing *E. coli* K12. Heretofore, transduction of *E. coli* during the stationary growth phase was unknown. I have discovered that in cultures of *E. coli*, such as χ1776, that are transduced poorly in the exponential growth phase, transduction can be accomplished in the stationary growth phase.

SUMMARY OF THE INVENTION

This invention provides a method for facilitating transduction of genetic markers into any strain of *E. coli*, such as *E. coli* K12 χ1776, that is transduced poorly in the exponential growth phase. This method comprises growing the recipient *E. coli* strain to the stationary phase, during which time the culture is susceptible to transduction, and carrying out transduction by standard procedures during the stationary phase, thereby introducing genetic markers into the *E. coli* strain.

Strains of *E. coli* K12 χ1776 modified by transduction using this method are useful tools for biological containment and are contemplated as a part of this invention.

DESCRIPTION OF THE DRAWING

The accompanying drawing shows transduction of χ1776 in different stages of growth. Cultures of χ1776 were samples at various times in the growth cycle. Time=O represents an intersection determined by extrapolation of the exponential and stationary portions of a growth curve. Cultures were transduced with P1 vir a at an moe of 4.0. The frequency of transduction, expressed as transductants per pfu, was determined by assaying for prototrophy for thymine and threonine. Prototrophs for thymine are indicated by a solid dot (●), and prototrophs for threonine are indicated by a circle (O).

DETAILED DESCRIPTION OF THE INVENTION

Cloning individual genes offers potential benefits for improving yields, producing products by more efficient processes and developing new products. Constructing biological chimeras with recombinant DNA requires containment barriers that effectively reduce the probability of escape to the environment. Specific genetic selection provides one of the most reliable methods of cloning desirable genes. This invention provides a method for transducing genetic markers into those strains of *E. coli* in which transduction is poor in the exponential growth phase.

This method is especially useful for *E. coli* K12 χ1776, a crippled strain which cannot survive outside the specific environment of the laboratory. *E. coli* K12 χ1776 is transduced very inefficiently by normal procedures because the strain is resistant to infection by many common coliphages. Derivatives of *E. coli* K12 χ1776 which contain useful genetic markers can be prepared by the method of this invention. Such strains will be especially useful because they will qualify for effective containment. Strains of *E. coli* K12 χ1776 which are modified by transduction using this method are, therefore, considered to be one embodiment of this invention.

The method of this invention involves growing the *E. coli* culture to the stationary phase and carrying out transduction during this phase. During the stationary growth phase of such an *E. coli* culture, there is a dramatic increase in efficiency of transduction.

There are two types of transduction—generalized and specialized. Generalized transduction implies that there is an ability for transduction of any given marker; specialized transduction implies that the phage can transmit only a limited region of a genome. Transduction as used herein refers to generalized transduction.

In carrying out the method of this invention, standard procedures for transduction may be used. The standard procedure for transduction involves exposing a recipient bacterial culture to a bacteriophage-lysate prepared on a suitable donor. The term lysate as used herein refers to the bacteriophage-lysate prepared by infecting a suitable bacterial donor as described in the art. Any donor which is susceptible to a phage, the lysate of which will infect the *E. coli* strain, can be used.

In carrying out transduction, the multiplicity of exposure can vary with different strains and is normally within a range from about 0.01 to about 10. To facilitate transduction, the most effective multiplicity of exposure can be determined by standard laboratory procedures. With χ1776, for example, to obtain the maximum frequency of transductants per pfu, an moe of 0.4 is preferable; to obtain a maximum frequency of transductants per cell, an moe of about 4 is preferable.

The bacteriophage-lysates most frequently used for transductions of this type are prepared from bacteriophage P1 or a derivative of P1. Examples of commonly used bacteriophages which are derivatives of P1 include P1 vir a, P1 Harris and P1 kc.

Variations in several experimental parameters for transduction, such as concentration of calcium or magnesium, time for absorbing bacteriophage and concentration of cells, do not significantly alter the frequency of transduction when using the method of this invention.

The method of this invention is applicable for the introduction of any genetic marker. Since markers with selectable phenotypes constitute the group most useful for the genetic selection of chimeras, this procedure will facilitate construction of strains for isolating recombinant DNA.

This invention is further illustrated by the following specific example.

EXAMPLE

Procedure

All bacterial strains were derivatives of *E. coli* K12 and are identified in Table I.

TABLE I

Strains of *E. coli* K12

| Strain | Relevant Phenotype |
| --- | --- |
| 3000 | Prototrophic |
| AB1157 | Multiple auxo-trophic markers |
| W3110 Δ (trp A-E-ton B) | trp auxotroph |
| W3110 trp R⁻ | Resistant to 5-methyltryptophan |
| W3110 trp B 9578 | trp auxotroph |
| MV12 | trp auxotroph |
| χ1776 | thr and thy auxotroph; EK2 biological containment |

Cultures were inoculated (1/100) from fresh cultures in the stationary phase of growth and grown in L-broth or L2-broth with gyratory agitation at 37° C. Viabilities were measured by spreading serial dilutions on the above media solidified with 1.5% agar (Bacto, Difco; designates L-agar or L2-agar). Top agar of these media contained 0.005 M $CaCl_2$, and 0.7% agar (Bacto). Minimal medium (designated as LDM) for χ1776 contained the following ingredients in 1.0 L:

| | |
| --- | --- |
| NaCl | 3.0 g |
| KCl | 0.2 g |
| $MgSO_4$ | 0.05 g |
| $KH_2PO_4$ | 1.5 g |
| $Na_2HPO_4$ | 4.0 g |
| L-threonine | 0.5 g |
| L-methionine | 0.37 g |
| L-aspartic acid | 0.25 g |
| diaminopimelic acid | 0.1 g |
| thymine | 0.04 g |
| biotin | 0.001 g |
| thiamine | 0.01 g |
| nicotinamide | 0.01 g |
| D-glucose | 5.0 g |

The pH was adjusted to 7.0. The LDM was solidified with 1.5% agar (Bacto). Minimal top agar contained 0.9% NaCl and 0.7% agar (Bacto).

Lysates of bacteriophage P1 vir a were prepared and titered by known procedures. Strain W3110 Δ(trp A-E ton B) did not produce plaques with P1 vir a. A plaque-forming mutant of P1 vir a (P1 vir a DM1) was isolated by standard procedures.

Cell suspensions to be transduced were prepared with approximately $4.1 \times 10^8$ cells (which equals 1.0 optical density (OD) units at 550 nm in L2-broth). Cells were harvested and resuspended in 1.0 ml. of solution containing 1.0% tryptone, 10% diaminopimelic acid, 4% thymine, 0.1% biotin, 1% nicotinamide and 1% thiamine in distilled water. The suspension was mixed with 1.0 ml. of a solution containing 0.015 M $CaCl_2$ and 0.03 M $MgSO_4$. Bacteriophage-lysate sufficient to obtain an optimum moe was diluted into 1.0 ml of L-broth and mixed with the suspension of cells. Transduction mixtures were incubated at 37° C. for 20 min.

Frequencies of transductants were measured in samples from transduction mixtures. The cells were washed with phosphate-buffered saline-Mg (7.0 g $Na_2HPO_4$, 3.0 g $KH_2PO_4$, 4.0 g NaCl, and 0.001 M $MgSO_4$ in 1.0 L distilled $H_2O$), serially diluted, and overlaid in 3.0 ml of minimal top agar onto LDM-agar with the appropriate nutritional additions or deletions.

Results

Attempts to transduce cultures of $\chi 1776$ in the exponential phase of growth gave variable unsatisfactory results. Therefore, cultures were examined for transduction and phage-sensitivity during different phases of growth.

Samples with approximately $4.1 \times 10^8$ cells were withdrawn at different stages of growth and treated with bacteriophage at an moe of 4. After adsorption for 20 min., the frequencies of transductants were analyzed. Transduction to prototropy for thymine or threonine exhibited dramatic changes when the cultures entered the stationary phase of growth. Transductants were not observable with sensitivities of detection less than $10^{-8}$ transductants per pfu during the exponential phase of growth. During the stationary phase of growth, however, there was an increase to $3-5 \times 10^{-6}$ transductants per pfu. This is summarized in the accompanying drawing.

Different mutants of E. coli K-12 as donors were tested by preparing lysates from five mutants and measuring transduction of E. coli K12 $\chi 1776$ to prototrophy for thymine or threonine. Analyses were performed in mixtures with an moe of 4; frequencies of transduction were calculated as transductants per $10^7$ cells. Although the frequencies differed over a range of approximately 300-fold for a single marker or approximately 600-fold when considering both markers, as the result in Table II demonstrate, all of the lysates yielded transductants.

TABLE II

| Transduction with Bacteriophage Grown on Different Donor Strains | | |
|---|---|---|
| | Transductants per $10^7$ Cells | |
| Host for Pl vir a | thy+ | thr+ |
| EcK12 3000 | 26.3 | 21.9 |
| EcK12 MV12 | 660 | 336 |
| EcK12 W3110 trp B 9578 | 39.5 | 12.8 |
| EcK12 W3110 trp R− | 39.5 | 15.4 |
| *EcK12 W3110 Δ (trp A-E-ton B) | 2.8 | 1.1 |

*Pl vir a does not grow on EcK12 W3110 Δ (trp A-E-ton B). Therefore, a host-range mutant was isolated and used with this donor.

Transduction to prototrophy involves introducing wildtype genes to replace mutant genes. Introduction of a mutant gene to replace a wildtype gene was tested with the lysate from E. coli K12 W3110 trp R−. The frequency of trp R− transductants was approximately 14 per $10^7$ cells when the samples were analyzed by plating on minimal medium that contained 5-methyl tryptophan (100 mcg/ml).

I claim:

1. A method of transducing genetic markers into strains of *Escherichia coli* K12 $\chi 1776$ which comprises growing the E. coli culture to the stationary growth phase and then transducing said markers into said E. coli strain in the stationary growth phase.

2. The method of claim 1 wherein transduction is accomplished with a lysate of bacteriophage P1 or of a derivative of bacteriophage P1.

3. The method of claim 2 wherein transduction is accomplished with a lysate of bacteriophage P1 vir a.

* * * * *